United States Patent
Houthoff et al.

(10) Patent No.: US 6,248,531 B1
(45) Date of Patent: Jun. 19, 2001

(54) TRANS-PLATINUM COMPOUND, AND DIAGNOSTIC KIT

(75) Inventors: Hendrik-Jan Houthoff, Amsterdam; Jan Reedijk, Leiden; Herman H. Volkers, Monnickendam; Robert Jochem Heetebrij, Utrecht, all of (NL)

(73) Assignee: Kreatech Biotechnology B.V., Amsterdam (NL)

( * ) Notice: Subject to any disclaimer, the term of this patent is extended or adjusted under 35 U.S.C. 154(b) by 0 days.

(21) Appl. No.: 09/402,735

(22) PCT Filed: Apr. 9, 1998

(86) PCT No.: PCT/NL98/00206

§ 371 Date: Dec. 21, 1999

§ 102(e) Date: Dec. 21, 1999

(87) PCT Pub. No.: WO98/45304

PCT Pub. Date: Oct. 15, 1998

(30) Foreign Application Priority Data

Apr. 10, 1997 (EP) .................................................. 97201066

(51) Int. Cl.⁷ ............................... C12Q 1/68; C07C 5/02; C07C 5/03; G01N 33/533

(52) U.S. Cl. ................................ 435/6; 585/272; 436/546

(58) Field of Search ................................ 435/6; 436/546; 585/277

(56) References Cited

FOREIGN PATENT DOCUMENTS

WO 96/35696 * 11/1996 (WO).

OTHER PUBLICATIONS

Kiscelere et al. "Trans–diammindicheorplatinum (II)–Modified Probes for detection of Picogram Susutities of DNA". Analytical Biochemistry, vol. 206, pp 43–49.*

* cited by examiner

*Primary Examiner*—Jezia Riley
(74) *Attorney, Agent, or Firm*—Hoffmann & Baron, LLP

(57) ABSTRACT

The present invention is concerned with a trans-platinum based compound for use in a method for labelling a bio-organic molecule, having formula (I), wherein A represents a reactive moiety for attachment to a label, D represents a reactive moiety for attachment to a bio-organic molecule, and X1 and X2 represent the same or different inert moieties.

34 Claims, No Drawings

TRANS-PLATINUM COMPOUND, AND DIAGNOSTIC KIT

BACKGROUND OF THE INVENTION

The invention relates to a trans-platinum based compound, to a diagnostic kit comprising said compound, and to a method for labeling a bio-organic molecule wherein use is made of said compound.

Platinum (coordination) compounds have been considered interesting molecules for a very long time. For a review of these compounds and their uses we refer to Reedijk et al. (Structure and Bonding, 67, pp. 53–89, 1987). Especially cis-platinum has received a lot of attention as an anti-tumor drug. This anti-tumor reactivity of platinum compounds originates from their having at least two reactive groups (preferable cis-oriented towards each other), which make it possible to cross-link DNA molecules, thereby inhibiting the replication of these DNA molecules.

A different use of cis-platinum compounds has been described in European patent application No. 95201197.1. Herein a method is disclosed for linking bio-organic molecules and labels through cis-platinum compounds, of which two coordination sites are occupied by two ends of a stabilizing bridge, such as an ethylene diamine group.

These known cis-platinum compounds are suitable for linking labels to several kinds of bio-organic molecules. Examples are (poly)-peptides, polynucleic acids and nucleotides.

The labeling of polynucleic acids, such as DNA molecules, is desirable for applications in fields such as recombinant DNA technology. In many cases, however, one wishes not to label the nucleic acid macromolecule, but to label a certain nucleotide and enzymatically build this into a polynucleic acid. This way, the location of the label on the resulting polynucleic acid can be influenced, which is not possible when a label is attached to the macromolecule.

It has been found, however, that nucleotides linked to a label by cis-platinum linkers are not satisfactorily built in into DNA molecules by DNA polymerase, if at all. Therefore, in order to use a cis-platinum linker for obtaining a labeled DNA molecule one has to label the macromolecule.

The available alternatives for labeling a nucleotide, which can be incorporated into a polynucleic acid are the more conventional methods of labeling. However, these conventional methods also have a major disadvantage as they are not suitable for labeling any nucleotide. In some cases, for instance when only a few residues of a certain nucleotide are present in a certain polynucleic acid, or when the terminating nucleotide residue of a polynucleic acid is to be labeled, it is desired to be able to label any nucleotide.

An example of such a conventional method has been described by Dale et al., Biochemistry, 14, (1975), 2447–2457, which method involves direct covalent mercuration as a labeling technique. Dale et el. report that cytosine and uracil may be mercurated at their C5-position under mild conditions. However, they also report that for adenine, thymine and guanine bases negative results were obtained.

Thus, there is a need for a universal linking system, which is excellent for linking labels and bio-organic molecules, including all different nucleotides, and which also makes it possible to enzymatically build in any nucleotide labeled through said linking system in a polynucleic acid in an efficient manner.

SUMMARY OF THE INVENTION

The present invention provides such a universal linking system. It has been found that a trans-platinum based compound, having the formula:

(I)

wherein A represents a reactive moiety for attachment to a label, D represents a reactive moiety for attachment to a bio-organic molecule, and X1 and X2 represent the same or different inert moieties, meets the above requirements for use in a method for labeling a bio-organic molecule.

DETAILED DESCRIPTION OF THE INVENTION

Surprisingly, linking labels to several kinds of bio-organic molecules by using the compound of the invention is at least as efficient as the known methods. Further, it has been found that nucleotides linked to a label by the compound of the invention may be built in into polynucleotides very efficiently.

Nucleotides can assume two conformations: the syn-conformation and the anti-conformation. Definitions of these conformations can be found in Saenger, "Principles of Nucleic Acid Structure", Springer-Verlag Inc., 1984. It is believed that for a nucleotide to be satisfactorily built in into e.g. a DNA molecule it has to be in an anti-configuration. In U.S. Pat. No. 4,711,955 it has been reported that altering of the normal anti-conformation of a nucleoside must be avoided, because otherwise the nucleotide derivatives are unacceptable as polymerase substrates. Thus nucleotides having a syn-conformation will not be enzymatically incorporated into a polynucleotide in an efficient manner, if at all.

Besides this, it is known from the above-mentioned publication by Saenger that the presence of a bulky group or substituent at the N7 position of a nucleotide, i.e. the position to which a metal coordinates most easily, induces a nucleotide to have a syn-conformation. Thus, it would be expected that a nucleotide having a platinum compound coordinated to its N7 position would be in a syn-orientation. Accordingly, it would be expected to be not possible to incorporate said nucleotide into a polynucleotide with good results.

It is therefore very surprising that nucleotides linked to a label by a trans-platinum based compound in accordance with the invention may be built in into polynucleotides in a highly efficient manner.

The moieties X1 and X2 in formula (I) are inert. This means, that these moieties are ligands that remain bonded to the platinum core during the labeling reactions, i.e. they are stable under physiological conditions. They may be different or the same and may be any group that shows no interfering interactions between them and the label, bio-organic molecule or any other compound to be used in the application of the labeling techniques.

In these moieties X1 and X2 resides another advantage of the invention compared to the cis-platinum linkers. In order to obtain a stable cis-platinum compound it is imperative that said compound comprises a stabilizing bridge. For the trans-platinum compounds such a stabilizing bridge is not necessary. Accordingly, the possible variations in structure for the trans-platinum compounds of the invention are more numerous. Thus, according to the invention the skilled person has many instruments at his disposal for obtaining the desired properties of the compound.

In a preferred embodiment, X1 and X2 are the same or different non-leaving ligands. This means, that they are groups which have a very small leaving group character. Most preferred examples thereof are $NH_3$, $NH_2R$, $NHRR'$, and $NRR'R''$ groups, wherein R, R' and R" either represent an alkyl group having from 1 to 6 carbon atoms, as these groups form very stable bonds to the platinum core.

Particularly preferred is the embodiment wherein X1 and X2 are both an $N(CH_3)_3$ group. The presence of the methyl groups has a positive effect in that they prevent conformational modifications of the substrate due to for instance hydrogen bonding of a label or bio-organic molecule to the inert moieties.

The reactive moieties A and D are chosen such that they are easily replaced by or substituted with a label or a dioorganic molecule respectively. It is preferred that A and D are chosen from the group of acetate, $NO_3^-$, $HCO_3^-$, $CO_3^{2-}$, $SO_3^-$, $Cl^-$, $I^-$, and other halogens. These groups are good leaving groups and are therefore easily replaced.

In a highly preferred embodiment, a spacer, such as an oligolysine or a polylysine, is used. In accordance with this embodiment, A and/or D in formula (I) comprises a spacer, which spacer comprises a chain having at least four atoms, which chain comprises an electron donating moiety on one end and a reactive moiety on the other end, wherein the chain is attached to the platinum through the electron donating moiety. To the spacer, a label or a bio-organic molecule may be attached by a reaction with the end of the chain which is the most distant end seen from the platinum.

The use of a spacer has the advantage that the distance between the label and the bio-organic molecule can be optimized, so that steric factors cannot be an obstacle to an efficient labeling reaction.

The electron donating moiety of the spacer is a preferably an amine group or a thiolate anion, because it has been found that these groups are capable of forming very strong bonds to platinum.

In a further preferred embodiment, the chain of the spacer comprises at least one heteroatom, preferably an oxygen atom, as this positively affects the hydrophilicity of the chain, which is an important aspect in physiological systems.

It is also possible to use a spacer that comprises a platinum atom. In this embodiment, the invention provides a bis-platinum compound for linking labels and bio-organic molecules. The second platinum can either have a cis or a trans orientation.

The spacer comprises preferably no more than 20 carbon atoms in the chain, which is preferably a non-branched chain, thus causing no steric hindrance. The reasons for this will be clear.

A highly preferred spacer is 1,8-diamino-3,6-dioxaoctane, herein referred to as Dadoo. Dadoo is a very flexible spacer having two primary amine groups and a size that makes it very suitable for use as a spacer according to the invention.

The labels that may be linked to a bio-organic molecule by the compound of the invention are not critical. In principle all labels which can be attached to a bio-organic molecule and are employed to date can be used. These labels may be radioactive labels, enzymes (which need reaction with a substrate to be detected), specific binding pairs components such as avidin, streptavidin or biotin, biocytin, iminobiotin, colloidal dye substances, fluorochromes (rhodamin, etc.) including Cy®-colourants, reducing substances (eosin, erythrosin, etc.), (coloured) latex sols, digoxigenin, metals (ruthenium), metal sols or other particulate sols (selenium, carbon and the like), dansyl lysin, Infra Red Dyes, coumarines (amino methyl coumarine), antibodies, protein A, protein G, etc. The invention has most benefits with bulkier labels such as biotin, avidin, streptavidin, and digoxygenin.

Cy®-colourants are preferred labels to be linked to bio-organic molecules by the compound of the invention. These labels can very suitably be used for a technique referred to as multi-colour labeling. The reason for this is that different colourants of this kind, while having different colours, are very much alike in chemical structure.

Almost every bio-organic molecule which contains an accessible sulfur or nitrogen atom can be linked to a label by the present compounds. Very suitable compounds to be labeled are proteins, peptides, DNA molecules, RNA molecules, and (oligo)-nucleotides.

The platinum binds very easily to the N7 position of nucleotides. This way DNA or RNA molecules, be it single stranded or otherwise can be easily detected. It also allows for the production of probes for hybridization techniques wherein unlabeled DNA/RNA molecules hybridize to the labeled probe. The platinum compounds hardly interfere with the hybridization, if at all.

The platinum compounds of the invention are also very suitable for attaching bio-organic molecules to solid surfaces such as nitrocellulose, nylon filters or microtiter plates.

Nucleotides modified by using a linker according to the invention and oligo- and polynucleotides into which the nucleotides have been built in, or oligo- and polynucleotides that have been directly modified using these novel platinum compounds may be used as probes in biomedical research, clinical diagnostics and recombinant DNA technology.

The wide variety of utilities are based upon the ability of the platinum compounds to form stable complexes with polypeptides which in turn can be detected either by means of detectable moieties which are attached to or which interact with the polypeptide. Some uses include detecting and identifying nucleic acid containing etiological agents, e.g. bacteria and viruses; screening bacteria for antibiotic resistance; screening animals for genetic disorders in relation to pharmaceutical effects; diagnosing genetic disorders, e.g. trisomy 21, sickle cell anemia: chromosomal karyotyping; and identifying tumor cells.

The invention also encompasses a diagnostic kit for detecting, determining and/or localizing biological substances of interest, comprising the platinum compound of the invention, optionally together with other suitable means for detection. The platinum compound in the kit may comprise one or more of a spacer, a label and a bio-organic molecule. Of course, the invention also encompasses a kit, wherein these components are present separately, i.e. in unbound form.

In a different embodiment, the invention is directed to a method for labeling bio-organic molecules wherein use is made of the compounds disclosed herein-above.

In a method for labeling a bio-organic molecule in accordance with this embodiment, a reactive moiety of a trans-platinum based compound, having the formula:

(I)

wherein A, D, X1 and X2 have the above meanings, is reacted with a label; and the other reactive moiety of said trans-platinum based compound is reacted with a bio-organic molecule or vice versa.

In a preferred method for labeling a bio-organic molecule, the label and/or bio-organic molecule are connected to the platinum through a spacer, which spacer comprises a chain having at least four atoms, which chain comprises an electron donating moiety on one end and a reactive moiety on the other end, wherein the chain is attached to the platinum through the electron donating moiety. This spacer may be any of the spacers disclosed herein-above.

Of course, the spacer(s), the label, the bio-organic molecule and the trans-platinum may be attached to each other in any order. For instance, the spacer(s) may first be attached to the platinum followed by reacting the obtained compound with label and bio-organic molecule, but it is also possible first to attach the spacer(s) to the label and/or bio-organic molecule before the reaction with the platinum compound.

In a highly preferred embodiment, the invention provides a method as described above wherein the bio-organic molecule is a nucleotide.

The invention will be elucidated by the following, non-restrictive examples.

EXAMPLE 1

Preparation of trans-diamminedichloro-platinum(II) (trans-[Pt(NH$_3$)$_2$Cl$_2$])

1 g of potassium tetrachloroplatinate was dissolved in 20 ml Milli-Q and 0.6 ml of concentrated HCl was added. The mixture was heated until boiling and 2.5 ml of a 25% solution of NH$_4$OH was added dropwise with swirling. The resulting solution was evaporated to about 10 ml. To the resulting pale yellow residue, 100 ml of 6N HCl was added, and the mixture was evaporated as above to a volume of 15–20 ml. The trans-diamminedichloro-platinum(II) was deposited as a fine yellow powder. After cooling in ice, the mixture was filtered, washed with three 10 ml portions of ice-cold water, ethanol and ether, and air-dried. The trans-diamminedichloro-platinum(II) was crystallized from a minimum amount of boiling 0.1 N HCl. The product was characterized by infrared spectroscopy.

EXAMPLE 2

Preparation of trans-platinum diammine-DigDadoo chloride (trans-[Pt (NH$_3$)$_2$(DigDadoo-NH$_2$) Cl] (NO$_3$))

30 mg of trans-[Pt(NH$_3$)$_2$Cl$_2$](0.1 mmol) was suspended in 25 ml of N,N'-dimethylformamide and 17 mg (0.1 mmol) of AgNO$_3$ was added to the mixture which was reacted for 16 hours at room temperature shielded from the light. The precipitated AgCl was filtered off and 3.4 ml was taken from the filtrate (3.9 mg (0.014 mmol) of the trans-[Pt(NH$_3$)$_2$(Cl) (NO$_3$)]) and incubated with 8 mg of DigDadoo (digoxygenin-1,8-diamino-3,6-dioxaoctane, 0.014 mmol, purchased from Boehringer Mannheim) for 48 hours at 40° C., shielded from the light. The N,N'-dimethylformamide was removed in vacuo and the remainder was stirred in CH$_2$Cl$_2$ whereupon a yellowish powder precipitated. The precipitated powder was filtered off, washed with CH$_2$Cl$_2$ and dried. The product was characterized by high resolution $^1$H-NMR.

EXAMPLE 3

Preparation of trans-platinum diammine-DigDadoo-2'-deoxyGuanosine-5'-triphosphate (trans-[Pt(NH$_3$)$_2$ (DigDadoo-NH$_2$) (dGTP-N7)]$^2$ )

12 mg trans-[Pt(NH$_3$)$_2$ (DigDadoo-NH$_2$)Cl](NO$_3$) (0.014 mmol) was dissolved in 2 ml of Milli-Q and 3 mg (0.006 mmol) of 2'-deoxyguanosine-5'-triphosphate was added. The pH of the mixture was adjusted to ~6 with 0.1 N NaOH and the reaction was performed for 24 hours at 50° C. shielded from the light. The mixture was lyophilized and the residue was applied to a preparative anion exchange chromatography column (Q-Sepharose 26/10, Pharmacia BioTech) and a gradient starting with 100% Milli-Q to 100% NH$_4$HCO$_3$ was applied. The appropriate fraction was collected, concentrated and lyophilized to remove NH$_4$HCO$_3$. The product was analyzed by high resolution $^1$H and $^{31}$P-NMR and by analytical FPLC-methods, anion exchange (MonoQ 5/5, Pharmacia BioTech) and reversed phase (PepRPC 5/5, Pharmacia BioTech). The product was converted into its tetralithium salt by passing it over a Dowex cation exchange column.

EXAMPLE 4

Preparation of trans-platinum diammine-Cy5®-chloride (trans- [Pt(NH$_3$) $_2$ (Cy5®-NH$_2$) Cl](NO$_3$))

7.9 mg Cy5 Monofunctional reactive dye (0.01 mmol) was dissolved in 5 ml of dry N,N'-dimethylformamide and reacted with an excess of ethylenediamine for 4 hours at room temperature in an inert atmosphere (argon). The N,N'-dimethylformamide and excess ethylenediamine were removed in vacuo. The residue was redissolved in 10 ml of N,N'-dimethylformamide and 3 mg (0.009 mmol) trans-[(Pt (NH$_3$)$_2$(Cl) (NO$_3$)]) was added. The mixture was stirred for 16 hours at 50° C., shielded from the light. The N,N'-dimethylformamide was removed in vacuo and the residue was stirred in CH$_2$Cl$_2$, whereupon the product precipitated. The precipitate was filtered off and dried in vacuo. The product was characterized by high resolution $^1$H-NMR.

EXAMPLE 5

Enzymatic incorporation of trans-[Pt(NH$_3$)$_2$ (DigDadoo-NH$_2$) (dGTP)] into pBR 322 DNA The enzymatic incorporation was performed by incubating the following mixture overnight at 37° C.:

| | |
|---|---|
| Denaturated DNA (1 µg) | 8.0 µl |
| dTTP (5.0 mM) | 0.8 µl |
| dCTP (5.0 mM) | 0.8 µl |
| dATP (5.0 mM) | 0.8 µl |
| dGTP (1.0 mM) | 2.6 µl |
| trans- [Pt(NH$_3$)$_2$(DigDadoo-NH$_2$) (dGTP) ] (1 mM) | 1.4 µl |

| | |
|---|---|
| High Prime Mixture* | 4.0 µl |
| Sterile demineralized water | 1.6 µl |
| Total | 20 µl |

*The High Prime Mixture contained Klenow polymerase and hexanucleotides in an optimized buffer.

The incubation was stopped by adding 2 µl of 0.2 M EDTA and the volume of the mixture was adjusted to 40 µl by adding sterile demineralized water. A filter hybridization was performed with a probe concentration of 25 ng/ml, using dentarued homologous DNA dotted on filterstrips with the following dilution range: 100pg, 30 pg, 3 pg, 1 pg, 0.3 pg, 0.1 pg, 0.03 pg, 0.01 pg and 0 pg. Detection was carried out with anti-Dig-AP (Fab fragments from an antidigoxigening antibody from sheep conjugated with alkaline phosphatase (AP))(1:10,000) and CDP-Star (chemiluminescent substrate). As a result 0.3 pg hybridization was observed.

EXAMPLE 6 trans- [Pt(NH$_3$)$_2$ (DigDadoo-NH$_2$) (dGTP)] Oligo tailing using Terminal Transferase The tailing reaction was performed by incubating the following mixture for 15 minutes at 37° C.:

| | | |
|---|---|---|
| Reaction buffer: | 1M potassium cacodylate, 0.125 M Tris-HCl, 1.25 mg/m; Bovine serum albumine pH 6.6 (25° C.) | 4 µl |
| COCl$_2$ solution (25 mM) | | 4 µl |
| oligo (20 pmol/µl) | | 5 µl |
| trans- [Pt(NH$_3$)$_2$(DigDadoo-NH$_2$) (dGET) ]/dATP* | | 1 µl |
| Terminal Transferase 50U/µl | | 1 µl |
| Sterile demineralized water | | 5 µl |
| Total | | 20 µl |

*Mixture of 9 µl of trans-[Pt(NH$_3$)$_2$(DigDadoo-NH$_2$) (dGTP)] (1 mMO and 1 µl dATP (100 mM)

The incubation was stopped by adding 2 µl of a mixture of 1 µl glycogen and 200 µl 0.2 M EDTA having a pH of 8.0. Subsequently, a purification was performed by precipitation from ethanol and a hybridization analogous to the filter hybridization described in Example 5 was performed. As a result 10 pg hybridiztion was observed.

EXAMPLE 7

Normal DNA labeling using trans-[Pt(NH$_3$)$_2$ (DigDadoo-NH$_2$)Cl](NO$_3$)

From a standard QC procedure, testing a range of different ratios, the following protocol was performed. A mixture of 2 µl DNA (2 µg), 2 µl trans-[Pt(NH$_3$)$_2$(DigDadoo-NH$_2$)Cl] (NO$_3$) (0.1 mg/ml) and 16 µl sterile demineralized water was incubated for 30 minutes at 85° C. The incubation was stopped by adding 5 µl 1% sodium diethyldithiocarbamic acid. In a filter hybridization, which was performed analogous to the hybridization described in Example 5, 3 pg hybridization was observed.

EXAMPLE 8

Ratio labeling of DNA by mixing painting probes that have been labeled independently Identical painting probes were labeled in independent reactions using Fluorescein (Flu) and Rhodamine (Rho). After labeling, independent probes were mixed using a ratio of 1:9, 1:5, 1:1, 5:1 and 9:1, respectively, and tested spot blot and by filter hybridization. Detection was performed by alkaline phosphatse conjugated antibodies raised against Flu and Rho, respectively. After detection, ratios of labeled painting probes appeared to be identical when compared with the ratio of input marker molecule.

EXAMPLE 9

Ratio labeling of DNA using a defined mixed input of trans- [Pt(NH$_3$)$_2$ (Dadoo-NH$_2$)Cl]NO$_3$ marker complexes in one reaction Probes were labeled using similar ratios as described in Example 8, with the exception that the probe DNA was incubated with a mixture of trans-[Pt(NH$_3$)$_2$(Dadoo-NH$_2$) Cl]NO$_3$ marker (Flu and Rho) complexes in one reaction tube. After detection by conjugated antibodies, it appeared that distribution of label occurred equimolar and that different marker molecules did not interfere with each other, nor did they affect each other negatively. All results were confirmed by microscopial analysis

What is claimed is:

1. A method for labeling a bio-organic molecule, comprising the steps of
   (i) providing a trans-platinum compound, having the formula:

wherein A and D represent reactive moieties that are the same or different, and X$_1$ and X$_2$ are the same or different and are selected from the group consisting of NH$_3$, NH$_2$R, NHRR' and NRR'R" groups wherein R, R' and R" each represent an alkyl group having from 1 to 6 carbon atoms;
   (ii) replacing one reactive moiety of said trans-platinum based compound with a label; and
   (iii) replacing the other reactive moiety of said trans-platinum based compound with the bio-organic molecule.

2. A method according to claim 1, wherein A and/or D are selected from the group consisting of acetate, NO$_3^-$, HCO$_3^-$, CO$_3^{2-}$, SO$_3^-$, Cl$^-$, I$^-$, and other halogens.

3. A method according to claim 1, wherein the label and/or the bio-organic molecule are connected to the platinum through a spacer.

4. A method according to claim 3, wherein the spacer comprises a chain having at least four atoms.

5. A method according to claim 4, wherein the chain comprises an electron donating moiety on one end and a reactive moiety on the other end, wherein one or both of the reactive moieties of the trans-platinum based compound is or are replaced by the electron donating moiety of the spacer(s) and wherein the reactive moiety of the spacer(s) is replaced with the label and/or bio-organic molecule.

6. A method according to claim 5 wherein the electron donating moiety is an amine group or a thiolate anion.

7. A method according to claim 5, wherein the chain further comprises at least one heteroatom.

8. A method according to claim 7, wherein the spacer comprises no more than 20 carbon atoms in the chain and wherein the chain is essentially non-branched.

9. A method according to claim 5, wherein the spacer is 1, 8-diamino-3,6-dioxaoctane.

10. A method according to claim 7, wherein the bio-organic molecule is selected from the group consisting of proteins, peptides, DNA molecules, RNA molecules, and nucleotides.

11. A method according to claim 10 wherein the bio-organic molecule is a nucleotide.

12. A method according to claim 7, wherein the label is selected from the group consisting of biotin, avidin, streptavidin, digoxygenin, and fluorochromes including Cy®-colourants.

13. A trans-platinum based compound having the formula:

wherein A and D represent a reactive moiety, and X1 and X2 represent $NH_2R$, NHRR' or NRR'R" groups wherein R, R' and R" each represent an alkyl group having from 1 to 6 carbon atoms.

14. A compound according to claim 13, wherein one of the reactive moieties is replaced by a label.

15. A compound according to claim 14, wherein one of the reactive moieties is replaced by a bio-organic molecule.

16. A compound according to claim 15, wherein the bio-organic molecule is a nucleotide.

17. A diagnostic kit for detecting, determining and/or localizing biological substances of interest, comprising a compound according to claim 16, and reagents suitable for detection.

18. A diagnostic kit according to claim 17, further comprising a means for detecting the label.

19. A trans-platinum based compound having the formula:

wherein A represents a reactive moiety, LABEL represents a label, and $X_1$ and $X_2$ represent non-leaving ligands that are the same or different.

20. A compound according to claim 19 wherein X1 and X2 are selected from the same or different group consisting of $NH_3$, $NH_2R$, NHRR' and NRR'R" groups, wherein R,R' and R" each represent an alkyl group having from 1 to 6 carbon atoms.

21. A trans-platinum based compound having the formula:

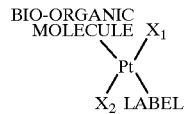

wherein BIO-ORGANIC MOLECULE represents a bio-organic molecule, LABEL represents a label, and $X_1$ and $X_2$ represent non-leaving ligands that are the same or different.

22. A compound according to claim 19 wherein X1 and X2 are selected from the same or different group consisting of $NH_3$, $NH_2R$, NHRR' and NRR'R" groups, wherein R, R' and R" each represent an alkyl group having from 1 to 6 carbon atoms.

23. A method for labeling a bio-organic molecule, comprising the steps of:

(i) providing a trans-platinum compound having the formula:

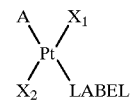

wherein A represents reactive moieties that are the same or different, LABEL represents a label, and $X_1$ and $X_2$ are the same or different, and are selected from the group consisting of $NH_3$, $NH_2R$, NHRR' and NRR'R" groups, wherein R, R' and R" each represent an alkyl group having from 1 to 6 carbon atoms; and (ii) replacing A with a bio-organic molecule.

24. A method according to claim 1, wherein A is selected from the group consisting of acetate, $NO_3^-$, $HCO_3^-$, $CO_3^{2-}$, $SO_3^-$, $Cl^-$, $I^-$, and other halogens.

25. A method according to claim 24, wherein the bio-organic molecule is connected to the platinum through a spacer.

26. A method according to claim 25, wherein the spacer comprises a chain having at least four atoms.

27. A method according to claim 26, wherein the chain comprises an electron donating moiety on one end and a reactive moiety on the other end, wherein A is replaced by the electron donating moiety of the spacer and wherein the reactive moiety of the spacer is replaced with the bio-organic molecule.

28. A method according to claim 27 wherein the electron donating moiety is an amine group or a thiolate anion.

29. A method according to claim 27, wherein the chain further comprises at least one heteroatom.

30. A method according to claim 27, wherein the spacer comprises no more than 20 carbon atoms in the chain and wherein the chain is essentially non-branched.

31. A method according to claim 27, wherein the spacer is 1, 8-diamino-3, 6-dioxaoctane.

32. A method according to claim 27, wherein the bio-organic molecule is selected from the group consisting of proteins, peptides, DNA molecules, RNA molecules, and nucleotides.

33. A method according to claim 32 wherein the bio-organic molecule is a nucleotide.

34. A method according to claim 27, wherein the label is selected from the group consisting of biotin, avidin, streptavidin, digoxygenin, and fluorochromes including Cy®-colourants.

* * * * *

UNITED STATES PATENT AND TRADEMARK OFFICE
CERTIFICATE OF CORRECTION

PATENT NO.   : 6,248,531 B1                                              Page 1 of 1
DATED         : June 19, 2001
INVENTOR(S)  : Houthoff et al.

It is certified that error appears in the above-identified patent and that said Letters Patent is hereby corrected as shown below:

<u>Column 9,</u>
Line 18, reads "...represent $NH_2$, $R_1NHRR$ or $NRR'R$"..." should read -- ...represent $NH_2R$, $NHRR'$ or $NRR'R$"... --.

<u>Column 10,</u>
Line 1, reads "A compound according to claim 19..." should read
-- A compound according to claim 21... --.

Signed and Sealed this

Sixteenth Day of July, 2002

Attest:

JAMES E. ROGAN
Attesting Officer          Director of the United States Patent and Trademark Office